(12) United States Patent
Kadokura et al.

(10) Patent No.: US 8,293,327 B2
(45) Date of Patent: Oct. 23, 2012

(54) PROCESS FOR FORMING THE STRONTIUM-CONTAINING THIN FILM

(75) Inventors: Hidekimi Kadokura, Sakado (JP); Shintaro Higashi, Tsurugashima (JP); Yoshinori Kuboshima, Tokyo (JP); Yumiko Kawano, Nirasaki (JP)

(73) Assignees: Kabushikikaisha Kojundokagaku Kenkyusho, Saitama (JP); Tokyo Electron Limited, Tokyo (JP)

( * ) Notice: Subject to any disclaimer, the term of this patent is extended or adjusted under 35 U.S.C. 154(b) by 575 days.

(21) Appl. No.: 12/145,831

(22) Filed: Jun. 25, 2008

(65) Prior Publication Data

US 2009/0004383 A1 Jan. 1, 2009

(30) Foreign Application Priority Data

Jun. 26, 2007 (JP) ................................. 2007-167166
May 29, 2008 (JP) ................................. 2008-140307

(51) Int. Cl.
*C23C 16/00* (2006.01)
*C07F 1/00* (2006.01)
(52) U.S. Cl. ................. 427/248.1; 260/665 R
(58) Field of Classification Search ................. 427/248.1
See application file for complete search history.

(56) References Cited

U.S. PATENT DOCUMENTS

| | | | |
|---|---|---|---|
| 5,552,181 A * | 9/1996 | Kondoh et al. | 427/248.1 |
| 6,231,658 B1 * | 5/2001 | Uchikawa et al. | 106/287.19 |
| 6,424,800 B1 * | 7/2002 | Kim | 392/388 |
| 6,475,902 B1 * | 11/2002 | Hausmann et al. | 438/627 |
| 2007/0120124 A1 * | 5/2007 | Chen et al. | 257/43 |
| 2008/0242111 A1 * | 10/2008 | Holme et al. | 438/778 |
| 2010/0291299 A1 * | 11/2010 | Cameron et al. | 427/255.6 |

FOREIGN PATENT DOCUMENTS

| | | |
|---|---|---|
| EP | 1645656 A1 | 4/2006 |
| JP | 62-186528 A | 8/1987 |
| JP | 02-225317 A | 9/1990 |
| JP | 2002-193981 A | 7/2002 |
| JP | 2002-525426 A | 8/2002 |
| JP | 2005-079118 A | 3/2005 |

OTHER PUBLICATIONS

"MOCVD & CVD Precursors," Strem; 1999; CVD Nov. 1999; p. 22.
Notification of Reasons for Refusal dated Aug. 20, 2012, issued in corresponding Japanese Patent Application No. 2008-140307, with English translation (5 pages).

* cited by examiner

*Primary Examiner* — Dah-Wei Yuan
*Assistant Examiner* — Jose Hernandez-Diaz
(74) *Attorney, Agent, or Firm* — Westerman, Hattori, Daniels & Adrian, LLP

(57) ABSTRACT

The present invention provides a process for forming a strontium-containing thin film of a cyclopentadienyl-based strontium compound, which is in the liquid state at room temperature to 50° C., can be purified by distillation, present as a monomer, has high vapor pressure, and suitable for mass production. bis(propyltetramethylcyclopentadienyl)strontium is used as an Sr source to form a strontium-containing thin film such as a $SrTiO_3$ film, a $(Ba, Sr)TiO_3$ film by chemical vapor deposition or atomic layer deposition.

9 Claims, 6 Drawing Sheets

PROCESS FOR FORMING THE STRONTIUM-CONTAINING THIN FILM

BACKGROUND OF THE INVENTION

1. Field of the Invention

The present invention relates to a process for forming a strontium-containing thin film by using a raw material suitable for forming a thin film containing strontium oxide or strontium sulfide by chemical vapor deposition (hereinafter, referred to as CVD) or atomic layer deposition (hereinafter, referred to as ALD).

2. Description of the Related Art

Films having high dielectric constant deposited by CVD and ALD such as films of $SrTiO_3$, $SrBi_2Ta_2O_9$, $SrBi_4Ti_4O_{15}$ are expected to serve as a dielectric for a highly integrated semiconductor device. A $SrRuO_3$ film is discussed for its use as a ferroelectric film electrode.

Conventionally, as for a raw material for forming these strontium-containing films by CVD and ALD, bis(dipivaloylmethanato)strontium ($Sr(C_{11}H_{19}O_2)_2$; hereinafter, referred to as $Sr(dpm)_2$) has been mainly discussed.

However, $Sr(dpm)_2$ has a problem in its supply, because it has a very low vapor pressure of 0.1 Torr/231° C. due to trimerization thereof.

Further, since it undergoes thermal decomposition at 230° C. or higher, it has a problem of simultaneous occurrence of thermal decomposition beyond control with desirable self-limited growth in film-forming by ALD.

There is therefore a need for an organostrontium compound having higher vapor pressure, higher reactivity with an oxidizer, and higher thermostability.

Examples of a candidate compound include a known compound, bis(pentamethylcyclopentadienyl)strontium ($Sr[C_5(CH_3)_5]_2$; hereinafter, referred to as $SrCP^*_2$). $SrCp^*_2$ is not an adduct coordinated with diethyl ether (($C_2H_5)_2O$; hereinafter, referred to as $Et_2O$) and tetrahydrofuran ($C_4H_8O$; hereinafter, referred to as THF).

These adducts have low thermal stability, release an added molecule by heating, are thermally denatured, and thus have unstable vapor pressure. These adducts also contain an oxygen atom, and can provide an oxygen atom through self-decomposition. These adducts are thus not preferred for use as the raw material in ALD.

In contrast, $SrCp^*_2$, which is not an adduct, is a monomer, has the highest vapor pressure among the organostrontium compounds, and immediately reacts with water as an oxidant. These properties are preferred for use as the raw material in ALD. In addition, since $SrCp^*_2$ has five methyl groups, it is more soluble in an organic solvent.

Therefore, the present inventors have disclosed a method for preparing $SrCP^*_2$ in Japanese Patent Application No. 2006-330359.

However, since $SrCP^*_2$ has a melting point of 207° C. and is in the solid state at room temperature, a sublimation step is required for final purification of $SrCp^*_2$ in the method. In addition, since $SrCp^*_2$ is a solid easily denatured by a trace amount of oxygen and/or water, it requires an expensive equipment and meticulous care.

Therefore, there is a need for a compound that can be purified by distillation, which is an effective purification method, and is in the liquid state at room temperature to 50° C. so that handling of the compound is easy under an inert atmosphere.

In other words, there is a need for a strontium compound that has a cyclopentadienyl group active to oxygen and water, does not contain ethers added thereto, present as a monomer, has high vapor pressure, has a group suitable for mass production, and is in the liquid state.

Now, a β-diketone based strontium complex such as the $Sr(dpm)_2$ is synthesized with metallic strontium as a raw material. However, since several ppms of Na and K are contained in the metallic strontium, several ppms of Na and K are contained in a crude compound as well.

Furthermore, a cyclopentadienyl-based strontium compound such as $SrCp^*_2$ is synthesized with an alkali metal compound such as $NaC_5(CH_3)_5$ (hereinafter referred to as $NaCp^*$) or $KC_5(CH_3)_5$ (hereinafter referred to as $KCp^*$) as a raw material; accordingly, in a crude compound, Na or K is contained much.

Since the β-diketone based strontium complex and $SrCp^*_2$ are in a solid state around room temperature, these are difficult to purify by distillation, that is, Na and K derived from the raw materials are difficult to remove efficiently.

Accordingly, it has been difficult to obtain a raw material for forming a strontium-containing thin film containing Na and K each at a content of 50 ppb or less. That is, there has been no raw material for forming a strontium-containing thin film, which is applicable to CVD and ALD and contains Na and K each at a content of 50 ppb or less.

The present inventors have thought that bis(propyltetramethylcyclopentadienyl)strontium ($Sr[C_5(CH_3)_4(C_3H_7)]_2$; hereinafter, referred to as $Sr(PrMe_4Cp)_2$) is preferable, because it can be prepared by using tetramethyl(n-propyl)cyclopentadiene ($C_5(CH_3)_4(C_3H_7)H$) having an analogous structure to pentamethylcyclopentadiene among commercially available cyclopentadiene compounds.

$Sr(PrMe_4Cp)_2$ is disclosed in European Patent Application Laid-Open No. 1645656, and is registered under CAS No. 882296-98-2.

In "MOCVD & CVD Precursors", Strem, 1999, CVD11/99, p. 22, a compound obtained by adding 1,2-dimethoxyethane ($CH_3OC_2H_4OCH_3$; hereinafter, referred to as DME) to $Sr(PrMe_4Cp)_2$ is described.

However, European Patent Application Laid-Open No. 1645656 describes only that an InAs film is grown at 600° C. by MOCVD using trimethylindium and monoethylarsine as raw materials in the presence of acatalytic amount (<0.25 mol %) of $Sr(PrMe_4Cp)_2$ in a table in Example 7. A trace amount of $Sr(PrMe_4Cp)_2$ is added as a catalyst and Sr is not substantially contained in the film. In addition, it does not describe about preparation and properties of $Sr(PrMe_4Cp)_2$.

"MOCVD & CVD Precursors", Strem, 1999, CVD11/99, p. 22, also does not describe $Sr(PrMe_4Cp)_2$ containing no ethers added thereto.

Cyclopentadienyl-based strontium compounds are prepared from compounds containing ethers added thereto, by removing the ethers. These compounds are difficult to be prepared without a route through ether adducts, and ethers added thereto are difficult to be removed.

Therefore, $Sr(PrMe_4Cp)_2$ has thus not been clearly described about its preparation and physical properties. A film containing Sr as a main ingredient has also not been formed from $Sr(PrMe_4Cp)_2$ as a raw material. In preparation of $Sr(PrMe_4Cp)_2$, key issues are a type of ether compound to be used and a method of removing ethers.

Furthermore, when Na is mingled only slightly in a semiconductor thin film forming material, an electric field at a semiconductor interface becomes irregular and a conductive thin film is corroded to largely damage the semiconductor characteristics; accordingly, a Na concentration in an organic strontium complex is demanded to be as near zero as possible. K as well is demanded to be as near zero as possible.

SUMMARY OF THE INVENTION

The present invention is directed to solve the technical problems described above. An object of the present invention is to provide process for forming a strontium-containing thin film using a raw material for forming a strontium-containing thin film of a cyclopentadienyl-based strontium compound, which is in the liquid state at room temperature to 50° C., can be purified by distillation, present as a monomer, has high vapor pressure, and suitable for mass production.

Further, the invention intends to provide a strontium-containing thin film where contents of Na and K are reduced.

The process for forming a strontium-containing thin film according to the present invention uses $Sr(PrMe_4Cp)_2$ for forming a thin film by CVD or ALD.

In a process for forming the thin film, $Sr(PrMe_4Cp)_2$ is preferably fed at a temperature from 130 to 350° C. by means of a bubbling method that uses an inert gas as a carrier gas.

The inert gas used at this time is preferably any one of Ar, $N_2$ and He and a flow rate thereof is preferably from 30 to 500 sccm.

Alternatively, in the process for forming the thin film, $Sr(PrMe_4Cp)_2$ may well be dissolved in a solvent to form a solution having the viscosity of 50 cP or less, followed by transporting to a vaporizer to vaporize at a temperature from 150 to 350° C., further followed by feeding.

A solvent used at this time is preferably any one of toluene, hexane and octane.

$Sr(PrMe_4Cp)_2$, which is the raw material for forming a strontium-containing thin film, is high in the vapor pressure and in a liquid state under room temperature, it maybe distilled and purified; accordingly, a content of each of Na and K that largely affect on the semiconductor characteristics is remarkably reduced in comparison with known strontium-containing thin film forming materials.

Therefore use of $Sr(PrMe_4Cp)_2$ obtained by the present invention allows for mass production of strontium-containing film by CVD and/or ALD.

Accordingly, a strontium-containing thin film where contents of Na and K are reduced may be formed.

DESCRIPTION OF THE PREFERRED EMBODIMENTS

Figure 1:
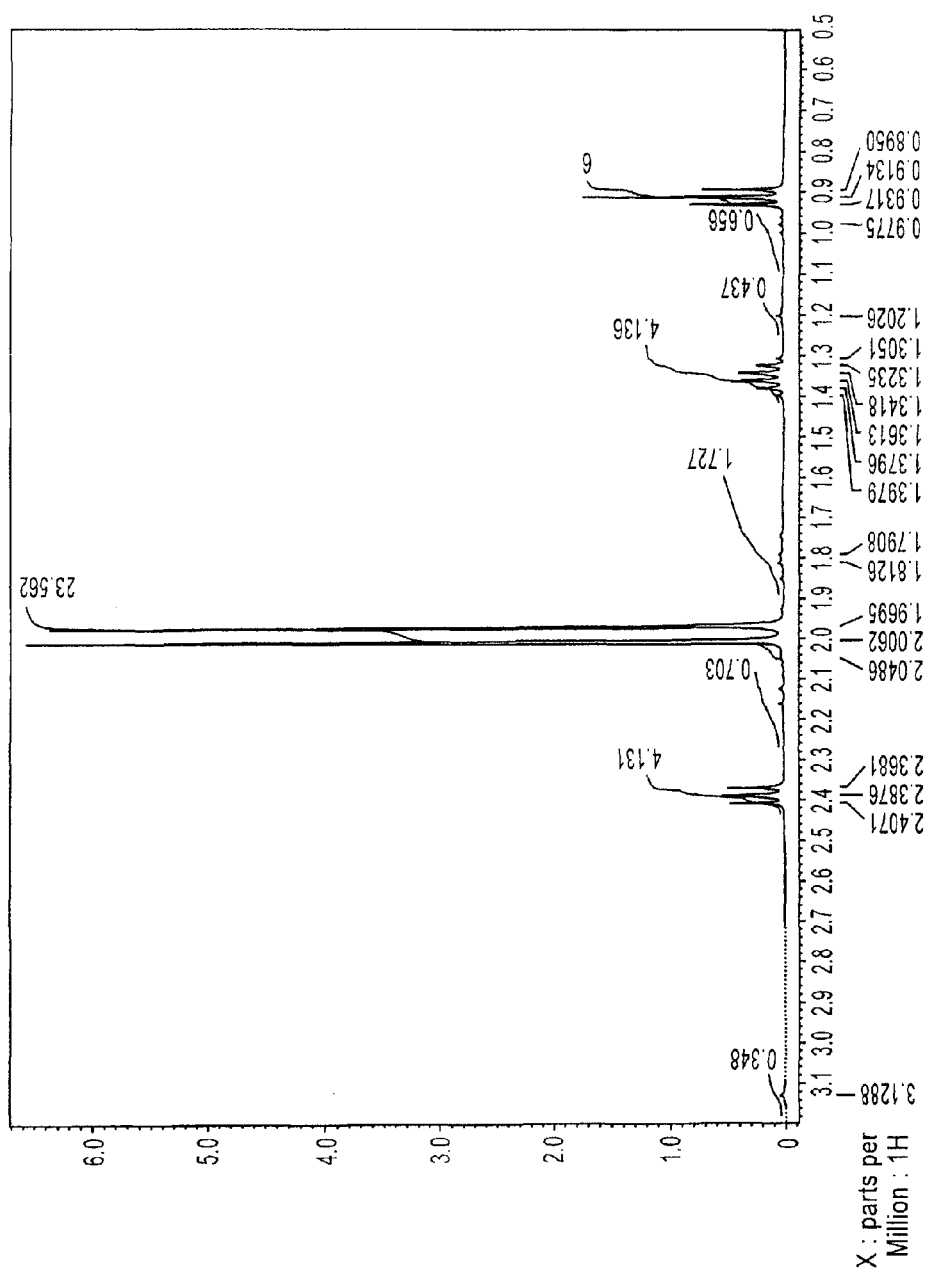
FIG. 1 shows a measured $^1$H-NMR spectrum of the twice distilled product in Example 1.

The present invention will be described below in detail.

The process for forming the strontium-containing thin film according to the present invention uses $Sr(PrMe_4Cp)_2$ for forming a thin film by CVD or ALD.

$Sr(PrMe_4Cp)_2$ as the raw material compound can be suitably prepared by the preparation process described below.

More particularly, $Sr(PrMe_4Cp)_2$ can be prepared by reacting $Na(PrMe_4Cp)$ or $K(PrMe_4Cp)$ with $SrI_2$ in THF to produce a THF adduct of $Sr(PrMe_4Cp)_2$; evaporating THF, and subjecting the residue to toluene extraction to give a toluene solution; evaporating toluene, and drying the residue under reduced pressure; heating to 100 to 160° C. in vacuo to remove THF by dissociation; and distilling to give $Sr(PrMe_4Cp)_2$.

The preparation process will be described in order below.

First, $Na(PrMe_4Cp)$ can be obtained by known methods, including a method of reacting commercially available propyltetramethylcyclopentadiene $(C_5(CH_3)_4(C_3H_7)H$; also referred to as: tetramethyl(n-propyl)cyclopentadiene) (Strem, AlfaAesar, etc.) with $NaNH_2$ in liquid $NH_3$ and a method of reacting the compound with NaH in THF or DME.

$K(PrMe_4Cp)$ can also be obtained by the similar methods.

Next, the obtained $Na(PrMe_4Cp)$ or $K(PrMe_4Cp)$ and anhydrous $SrI_2$ are dissolved in THF that is a reaction solvent for $Sr(PrMe_4Cp)_2$ preparation. The reaction undergoes easily to produce an adduct of $Sr(PrMe_4Cp)_2$ (THF).

It is noted that DME is not suitable, because when DME is used as a reaction solvent, although an adduct of $Sr(PrMe_4Cp)_2(DME)$ generates easily, DME is difficult to be removed therefrom as shown in the following Comparative Example 1.

Diethyl ether is also not suitable, because when diethyl ether is used as a solvent, solubility of a reaction raw material thereto is small, a reaction rate is slow, and volumetric efficiency is not good.

After the reaction ends, the THF solvent is evaporated, and an adduct of $Sr(PrMe_4Cp)_2(THF)$ is extracted with toluene. Since the adduct is well dissolved in toluene but sodium iodide and potassium iodide produced as bi-products are insoluble therein, the extraction is easy.

Toluene of a toluene solution obtained by the extraction is evaporated, and the residue is dried under reduced pressure to give an adduct of $Sr(PrMe_4Cp)_2$ (THF). The THF adduct has a melting point of about 130° C.

The adduct is heated to 100 to 160° C. under vacuum of 0.001 to 0.1 Torr to bring the content in the reaction pot to the melt state. In this state, dissociated THF is trapped in a deep cold trap. When increase of accumulation in the trap is no longer observed, a distillation operation is conducted under 160 to 180° C./0.01 to 0.1 Torr to distill $Sr(PrMe_4Cp)_2$.

$Sr(PrMe_4Cp)_2$ thus obtained is a viscous liquid without solidifying at room temperature.

Use of $Sr(PrMe_4Cp)_2$ obtained by the method described above as a raw material allows for stable formation of strontium-containing oxide film, sulfide film, and the like by CVD and ALD.

Furthermore, according to a producing process described above, $Sr(PrMe_4Cp)_2$ that contains each of Na and K by 50 ppb or less is obtained.

Accordingly, when, by use of $Sr(PrMe_4Cp)_2$ that is obtained according to a producing process described above and less contains K and Na as a raw material, strontium-containing thin films such as a $SrTiO_3$ film, a $(Ba, Sr)TiO_3$ film and a $SrRuO_3$ film are formed, the respective contents of K and Na in the thin film may be reduced more than ever.

Examples of a method for supplying $Sr(PrMe_4Cp)_2$ in film formation include a method comprising heating $Sr(PrMe_4Cp)_2$ to 130 to 170° C. to make it fluid liquid and bubbling a carrier gas into it to vaporize, and a method comprising dissolving $Sr(PrMe_4Cp)_2$ in an inert hydrocarbon solvent, supplying the solution with a liquid mass flow meter, and making the total solution vaporize with a vaporizer at 150 to 350° C.

When $Sr(PrMe_4Cp)_2$ is fed by bubbling, a cylinder temperature may be set at, without restricting temperatures of examples below, a temperature from 130 to 350° C. A carrier gas at this time may well be an inert gas and, other than Ar, $N_2$ and He may be used. Furthermore, while, when a flow rate thereof is too small, vapor is not transported, when the flow rate is excessive, cylinder internal pressure is raised to disturb vaporization of a raw material; accordingly, the flow rate is preferably from 30 to 500 sccm.

Furthermore, when $Sr(PrMe_4Cp)_2$ is dissolved in a solvent to lower the viscosity and liquid transported to a vaporizer to vaporize, the viscosity may well be 50 cP or less without restricting to that of the examples. When the viscosity is in the range, a risk of clogging a piping and the inside of the vaporizer may be lowered.

The solvent used is preferably toluene having the highest solubility. However in the case that a concentration of the solution maybe low, not only toluene but hexane and octane having a relatively good solubility may be used.

Use of vapor of $Sr(PrMe_4Cp)_2$ generated by such a method as described above, vapor of titanium compound such as $Ti(OiPr)_4$, $Ti(OtBu)_4$, $Ti(NMe_2)_4$, $Ti(NEtMe)_4$, or $Ti(NEt_2)_4$, and an oxidant such as oxygen, ozone, or water allows for formation of a $SrTiO_3$ film by CVD or ALD.

Further, use of mixed vapor of $Sr(PrMe_4Cp)_2$ and $Ba(PrMe_4Cp)_2$, vapor of titanium compound such as $Ti(OiPr)_4$, $Ti(OtBu)_4$, $Ti(NMe_2)_4$, $Ti(NEtMe)_4$, or $Ti(NEt_2)_4$, and an oxidant such as oxygen, ozone, or water allows for formation of a $(Ba,Sr)TiO_3$ film by CVD or ALD.

Furthermore, use of vapor of $Sr(PrMe_4Cp)_2$, vapor of ruthenium compound such as $Ru(EtCp)_2$, and an oxidant such as oxygen, ozone, or water allows for formation of an $SrRuO_3$ film by CVD or ALD.

EXAMPLES

The present invention will be further described in detail with reference to Examples, but is not limited by the Examples.

Example 1

Preparation of $Sr(PrMe_4Cp)_2$

The inside of 1L three-neck flask equipped with a thermometer, a stirrer, an inlet, and a reflux condenser was substituted with argon in vacuo. In the flask, 75 g (0.40 mol) of $Na(PrMe_4Cp)$ was dissolved in 600 ml of THF, which had been dehydrated and deoxygenated. To this was added 72 g (0.21 mol) of powder $SrI_2$ with ice-cooling the flask, and then stirred for 8 hours at 40° C.

The solvent was removed under reduced pressure. The reaction mixture was dried, 600 ml of toluene which had been dehydrated and deoxygenated was added, and the mixture was stirred with heating to extract. The reaction mixture was allowed to stand, and filtered to give a clear filtrate. Toluene was removed under reduced pressure. The residue was dried at 100° C. under reduced pressure to give 89 g of pale yellow solid (initial dried product) having a melting point of about 130° C.

The solid was charged in a high vacuum distillation equipment, and held at 110 to 160° C./0.1 to 0.01 Torr for one hour. During this time, THF of the THF adduct gradually dissociated and was trapped in a deep cold trap to an amount of 8.1 g. A temperature of the system was gradually elevated. A trace amount of initial crystal fraction was removed. A main fraction was collected at 170 to 180° C./0.1 to 0.01 Torr to give 61 g of pale yellow viscous liquid.

The viscous liquid was charged in the a high vacuum distillation equipment again, and held at 100 to 160° C./0.1 to 0.01 Torr for one hour to remove a trace amount of residual THF, and then distilled at 170 to 180° C./0.01 to 0.1 Torr to give 56 g of pale yellow viscous liquid (twice distilled product) as a main fraction.

The twice distilled product was identified as $Sr(PrMe_4Cp)_2$ (0.136 mol) by the following analysis. The yield was 68% to $Na(PrMe_4Cp)$.

Methods and results of identification analysis and physical property evaluation for twice distilled product are described below.

(1) Composition Analysis

A liquid produced by wet decomposition was analyzed by ICP emission spectroscopy. A content of Sr was 20.7% (theoretical value: 21.15%).

For impurities, results were: Ca=1900, Mg<50, Ba=10000, Na<50, K<50, Cr<50, Fe<50, Cu<50, Ni<50 (unit: ppb)

(2) $^1$H-NMR

Measurement condition (equipment: JNM-ECA400 (400 MHz), solvent: $C_6D_6$, method: 1D)

FIG. 1 shows a measured spectrum of the twice distilled product. For comparison, FIG. 2 shows a measured spectrum of the initial dried product.

Considering positions of signals, the number of H, ratios of the number of H in $Sr(PrMe_4Cp)_2$ to the number of H in THF in FIGS. 1 and 2, δH (ppm) were assigned as follows.

2.01(s), 1.97(s)12H: two $CH_3$ groups away from —$C_3H_7$ in $C_5(CH_3)_4$ and two $CH_3$ groups near —$C_3H_7$ in $C_5(CH_3)_4$ 2.39(t)2H: $CH_2CH_2CH_3$ 1.36(m)2H: $CH_2CH_2CH_3$ 0.92(t)3H: $CH_2CH_2CH_3$ 3.14(t), 1.21(m): —$OCH_2CH_2CH_2CH_2$— in THF From the measured spectrum shown in FIG. 1, in the twice distilled product, the number of mole of THF added to one mole of Sr was calculated as (0.348+0.437)/(23.562+4.131+4.136+6)×38/8=0.09. An average formula was $Sr(PrMe_4Cp)_2(THF)_{0.09}$. The twice distilled product had a trace amount of THF coordinated thereto, but can be substantially considered as $Sr(PrMe_4Cp)_2$.

Figure 2:
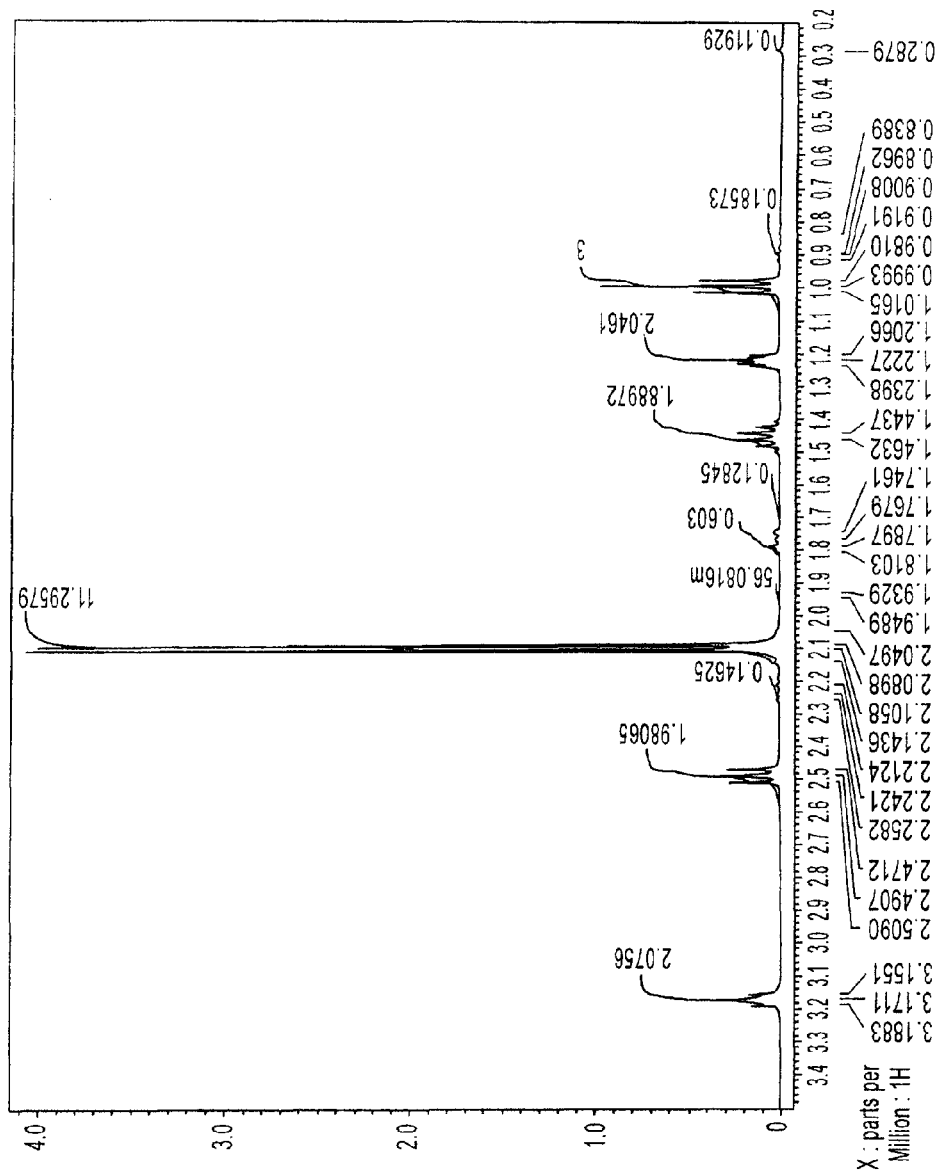
FIG. 2 shows a measured $^1$H-NMR spectrum of the initial dried product in Example 1.

From the measured spectrum shown in FIG. 2, in the initial dried product, the number of mole of THF added to one mole of Sr was calculated as (2.076+2.046)/(11.296+1.981+1.890+3)×38/8=1.08. An average formula was $Sr(PrMe_4Cp)_2(THF)_{1.08}$.

An actual content of Sr in the initial dried product was 18.1%, while a theoretical content of Sr in $Sr(PrMe_4Cp)_2(THF)_1$ is 18.02%.

The initial dried product was thus considered as $Sr(PrMe_4Cp)_2$ containing about one molecule of THF added thereto.

(3) Property and Melting Point

The twice distilled product was pale yellow, and very viscous liquid at room temperature. Its viscosity was about 1000 poises.

(4) TG-DTA

Measurement condition (sample weight: 14.40 mg, atmosphere: Ar 1 atmosphere, temperature rising rate: 10.0 deg/min)

Figure 3:
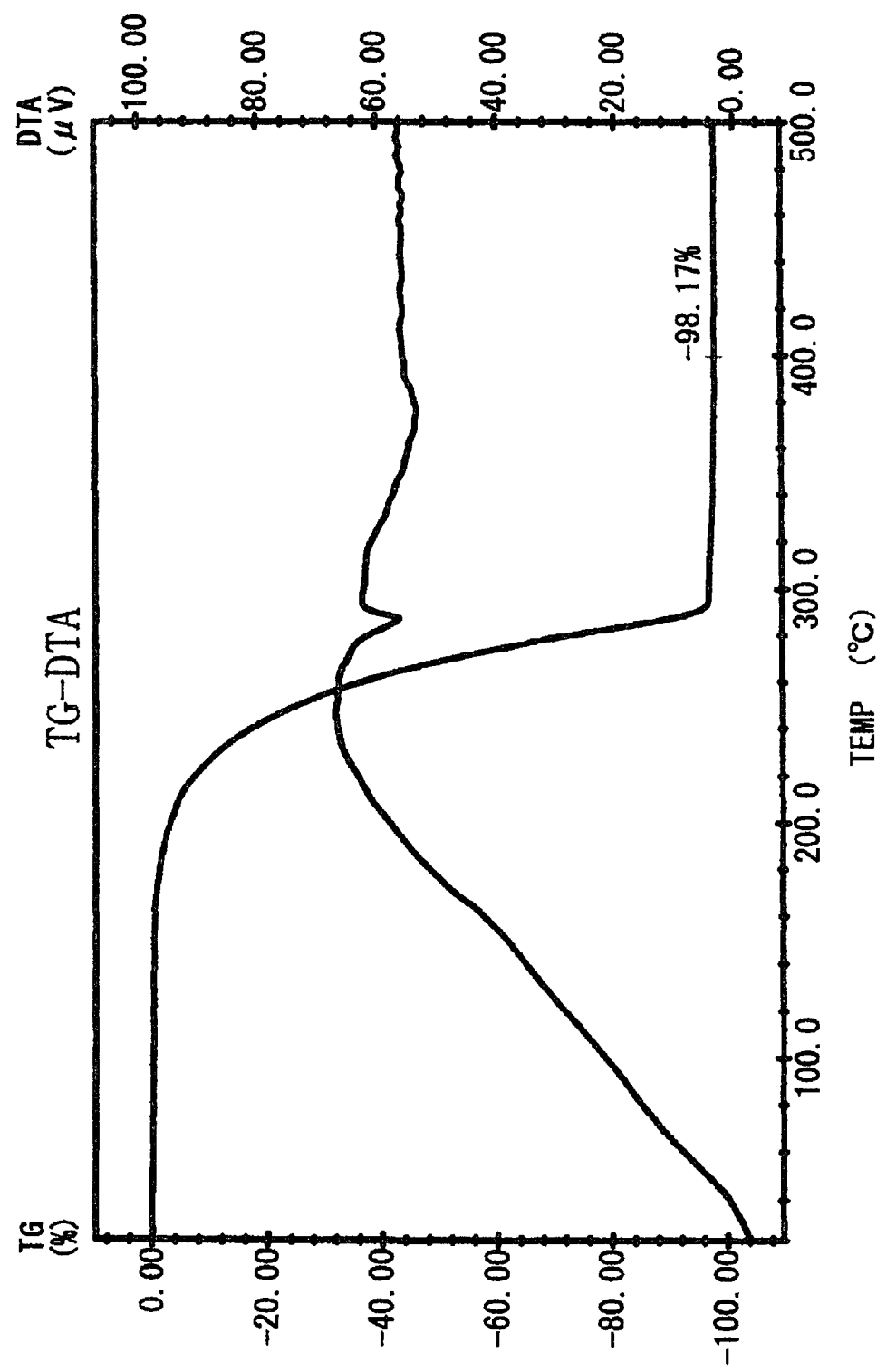
FIG. 3 shows a measured TG-DTA curve at one pressure of the twice distilled product in Example 1.

FIG. 3 shows a measured curve of the twice distilled product. For comparison, FIG. 4 shows a measured curve of the initial dried product.

Figure 4:
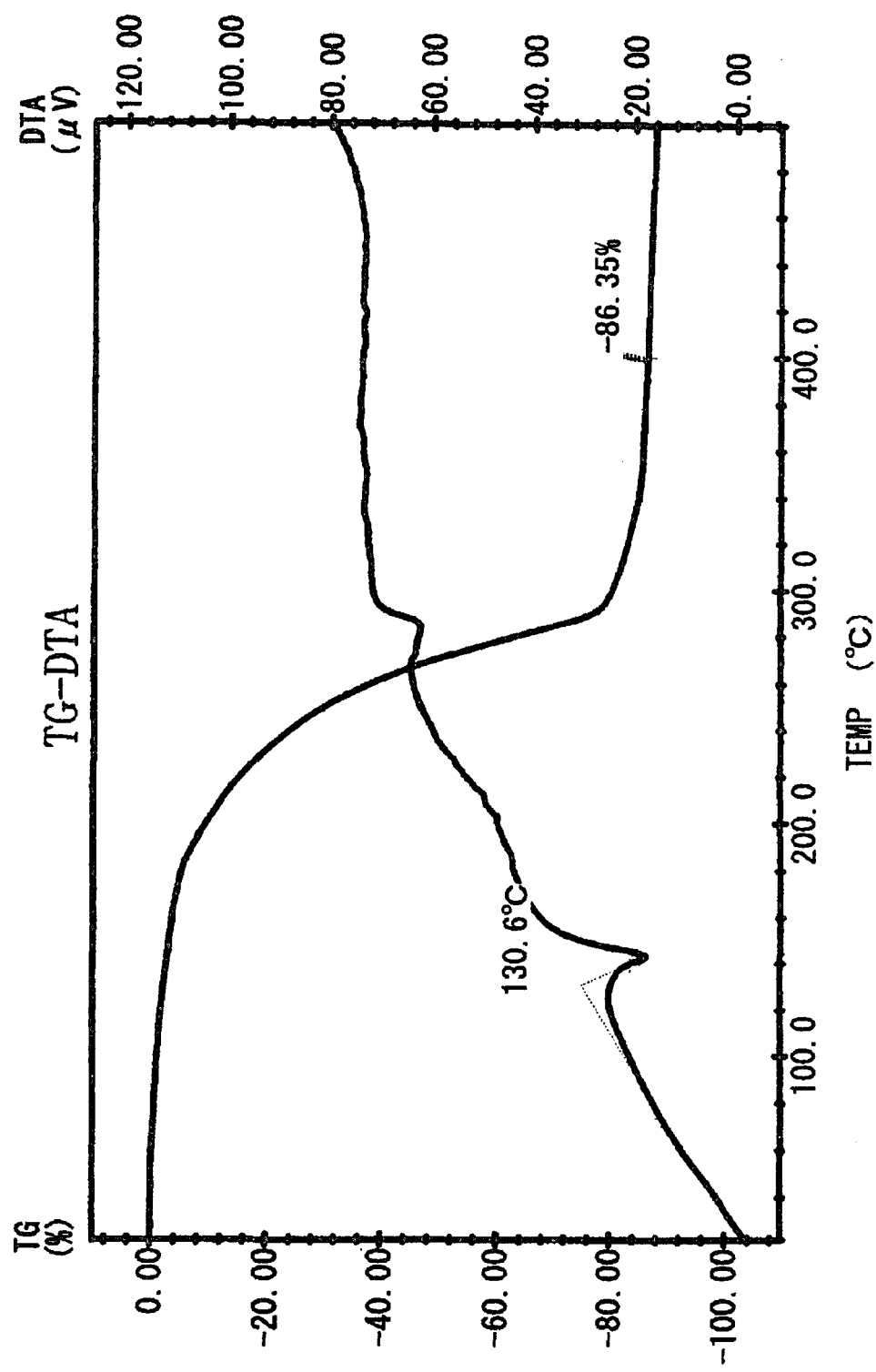
FIG. 4 shows a measured TG-DTA curve at one pressure of the initial dried product in Example 1.

It is estimated form TG-DTA curves shown in FIGS. 3 and 4 that the twice distilled product did not contain THF to be removed, because it did not lose its weight until around 160° C.

It is also shown that the twice distilled product was vaporized by 97% before 300° C., and thus is not thermally deteriorated at 300° C. or lower in a short time at the minute order, and has thermostability required for use as a raw material for ALD and CVD.

(5) Vapor Pressure

A result of a vapor saturation methodology was 0.1 Torr/ 170° C.

(6) Density

A density was 1.2 g/cm$^3$ (30° C.).

(7) Solubility

Solubilities in 1L each of solvents at room temperature were: 350 g for toluene; 280 g for THF; 70 g for hexane; and 70 g for octane.

It was confirmed that the twice distilled product has high solubility in toluene, and relatively high solubility in octane and the like.

Comparative Example 1

Preparation of Sr(PrMe$_4$Cp)$_2$ using DME as a Solvent

The inside of 300 mL three-neck flask equipped with a thermometer, a stirrer, an inlet, and a reflux condenser was substituted with argon in vacuo. In the flask, 16 g (0.086 mol) of Na(PrMe$_4$Cp) was dissolved in 160 ml of DME, which had been dehydrated and deoxygenated. To this was added 15.5 g (0.045 mol) of powder SrI$_2$ with ice-cooling the flask, and then stirred for 8 hours under a reflux condition.

The solvent was removed under reduced pressure. The reaction mixture was dried, 200 ml of toluene which had been dehydrated and deoxygenated was added, and the mixture was stirred with heating to extract. The reaction mixture was allowed to stand, and filtered to give a clear filtrate. Toluene was removed under reduced pressure. The residue was dried at 100° C. under reduced pressure to give 18.5 g of product, which was at first a pale yellow liquid and turned into a solid having a melting point of about 100° C. after one day.

The solid was charged in a high vacuum distillation equipment, and held at 110 to 160° C./0.1 to 0.01 Torr for one hour. During this time, DME of the DME adduct gradually dissociated and was trapped in a deep cold trap to an amount of 1.2 g. A temperature of the system was gradually elevated. A trace amount of initial fraction was discarded. A main fraction was collected at 170 to 175° C./0.1 to 0.01 Torr to give 14.7 g of pale yellow solid (once distilled product) that solidifies at room temperature (melting point: about 50 to 80° C.).

The solid was charged in the a high vacuum distillation equipment again, and held at 100 to 160° C./0.1 to 0.01 Torr for one hour. A temperature of the system was elevated. A main fraction was collected at 170 to 175° C./0.01 to 0.1 Torr to give 12.8 g of product (twice distilled product), which was collected as a liquid and turned into a pale yellow solid that solidifies at room temperature (melting point: about 50 to 80° C.).

The twice distilled product was similarly subjected to $^1$H-NMR and TG-DTA measurements as in Example 1.

(1) $^1$H-NMR

Figure 5:
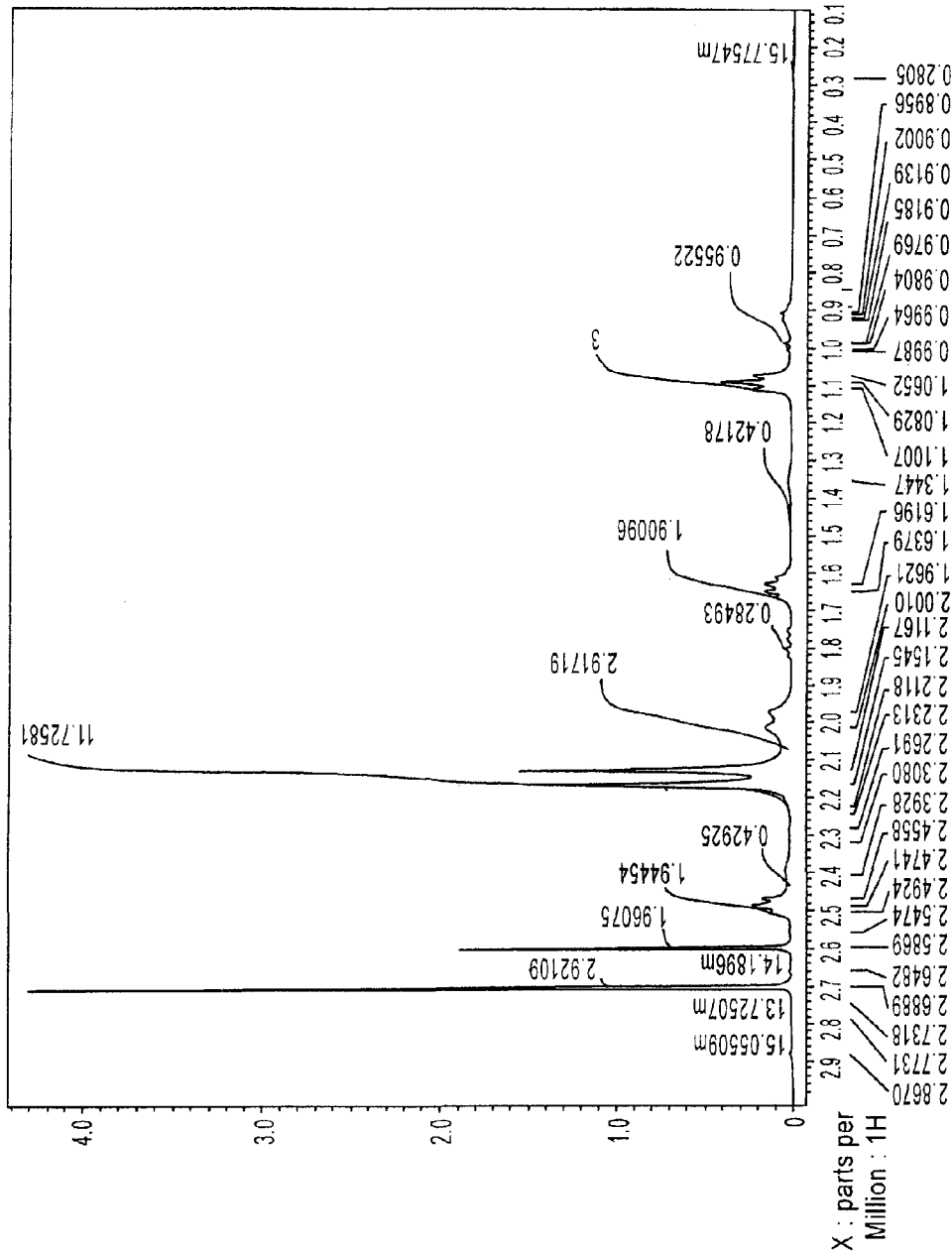
FIG. 5 shows a measured $^1$H-NMR spectrum of the twice distilled product in Comparative Example 1.

FIG. 5 shows a measured spectrum of the twice distilled product.

Considering positions of signals, the number of H, ratio of the number of H in Sr(PrMe$_4$Cp)$_2$ to the number of H in DME, δH (ppm) were assigned as follows.

2.15 (s), 2.12 (s)12H: two CH$_3$ groups away from —C$_3$H$_7$ in C$_5$ (CH$_3$)$_4$ and two CH$_3$ groups near —C$_3$H$_7$ in C$_5$ (CH$_3$)$_4$ 2.47(t)2H: CH$_2$CH$_2$CH$_3$ 1.63(m)2H: CH$_2$CH$_2$CH$_3$ 1.08(t)3H: CH$_2$CH$_2$CH$_3$ 2.69(t), 2.59 (m): CH$_3$OCH$_2$CH$_2$OCH$_3$ in DME From the measured spectrum shown in FIG. 5, in the twice distilled product, the number of mole of DME added to one mole of Sr was calculated as (2.921+1.961)/(11.726+1.945+1.901+3)×38/10=1.00. An average formula was Sr(PrMe$_4$Cp)$_2$(DME)$_{1.00}$.

There were many signals derived from impurities in FIG. 5, which suggests that the adduct undergoes thermal decomposition during distillation with heating.

An actual content of Sr in the twice distilled product was 18.2%, while a theoretical content of Sr in Sr(PrMe$_4$Cp)$_2$ (DME)1 is 17.37%.

It was confirmed that DME was difficult to be removed from the DME adduct by vacuum heat distillation.

(2) TG-DTA

Figure 6:
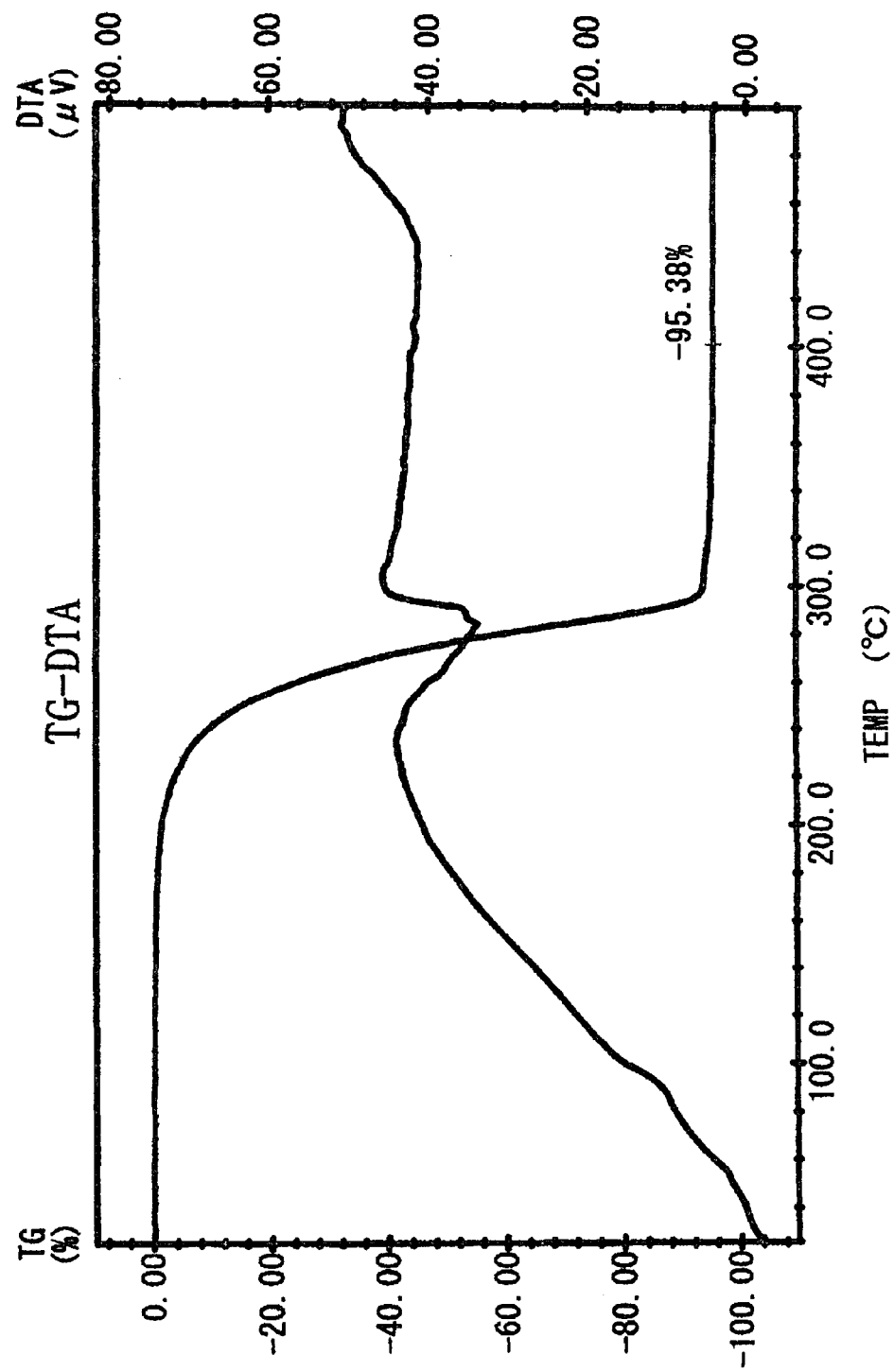
FIG. 6 shows a measured TG-DTA curve at one pressure of the twice distilled product in Comparative Example 1.

FIG. 6 shows a measured curve of the twice distilled product.

It is estimated from TG-DTA curves shown in FIG. 6 that there was no sign of DME dissociation and most of the twice distilled product vaporized as a DME adduct.

From the results of $^1$H-NMR and TG-DTA measurements, the twice distilled product was found not to release DME by heating but to vaporize mainly as a DME adduct.

That is, the method for preparing Sr(PrMe$_4$Cp)$_2$ via DME adduct using DME as a solvent cannot prepare pure Sr(PrMe$_4$Cp)$_2$.

It is therefore difficult to produce pure Sr(PrMe$_4$Cp)$_2$ from commercially available Sr(PrMe$_4$Cp)$_2$ (DME).

Comparative Example 2

Production of SrCp*$_2$ with NaCp* as a Raw Material

Into a 1 L three-neck flask equipped with a thermometer, a stirrer, an inlet and a gas outlet, after vacuum with argon replacement, 750 ml of dehydrated and deoxygenated THF and 79 g (0.50 mol) of NaCp* are charged and dissolved, and, while the flask is cooled with water, 90 g (0.246 mol) of SrI$_2$ powder is added, followed by agitating at a temperature from 25 to 40° C. for 24 hr.

In the next place, a solvent is removed under reduced pressure, followed by drying, 900 ml of dehydrated and deoxygenated toluene is added to extract under heating and agitation, after standing still, followed by filtering, and thereby a transparent filtrate is obtained. From the filtrate, toluene is distilled away under reduced pressure, followed by drying at 100° C. under reduced pressure. A solid content is taken out in a globe box and slightly pulverized, and, thereby 98 g of pale yellow fluent powder is obtained.

The powder is charged in a sublimating unit and a first sublimation is carried out at 140 to 180° C./0.1 Torr, and thereby, 65 g of a first sublimated matter is obtained.

Then, the first sublimated matter is charged in a sublimating unit and a second sublimation is carried out at 140 to 180° C./0.1 Torr, and, thereby, 62 g of a second sublimated matter is obtained.

The crystal of the second sublimated matter is identified, as a result of an analysis described below, to be SrCp*$_2$ (0.162 mol), and the yield thereof is 69% relative to NaCp*.

Solid matters obtained in the respective steps are subjected to, similarly to example 1, a composition analysis due to ICP emission spectroscopy and $^1$H-NMR measurement.

As the result thereof, from a Sr content analysis value (theoretical value 24.47%) and a ratio of a number of H of a total SrCp*$_2$ signal of $^1$H-NMR and a number of H of THF signal, an average chemical formula is assumed as shown below.

Product dried under reduced pressure: Sr content 19.7%, SrCp*$_2$(THF)$_{1.5}$

First sublimated matter: Sr content 22.1%, SrCp*$_2$(THF)$_{0.5}$

Second sublimated matter: Sr content 25.3%, SrCp*$_2$

Furthermore, the second sublimated matter is subjected to ICP emission spectroscopy and impurities are found to be Ca=2800, Mg<50, Ba=29000, Na=940, K<50, Cr<50, Fe<50, Cu<50 and Ni<50 (unit: ppb). In comparison with example 1, Na is contained much.

Comparative Example 3

Production of SrCp*$_2$ with KCp* as a Raw Material

Except that, in place of NaCp*, KCp* is used, according to a process similar to that of comparative example 2, a synthesis is carried out with the same mole of a raw material.

The yield of SrCp*$_2$ is 65% to KCp*.

Similarly to the example 1, a second sublimated matter is subjected to a composition and impurity analysis due to the ICP emission spectroscopy.

As the result, an analysis value of Sr content is 25.0% (theoretical value 24.47%) and impurities are found to be Ca=3000, Mg<50, Ba=31000, Na<50, K=1100, Cr<50, Fe<50, Cu<50 and Ni<50 (unit: ppb). In comparison with example 1, K is contained much.

Comparative Example 4

Production of Sr(dpm)$_2$

Into a 500 ml four-neck flask equipped with a thermometer, an agitation blade and a reflux unit, after vacuum with argon replacement, 350 ml of toluene is charged, followed by charging 65.6 g (356 mmol) of dipyvaloylmethane (dpmH) and 7.8 g (89 mmol) of metallic strontium, further followed by heating under agitation. After a 24 Hr's reaction under reflux, a metal chip is disappeared.

In the next place, under reduced pressure, a solvent and unreacted dpmHs are distilled away. Furthermore, under 130° C. and 0.05 Torr, dpmH slightly dissolved is distilled away.

Of the residue, 34 g is charged in a high vacuum distilling unit and distilled under 230° C./0.02 Torr, thereby 30 g of Sr(dpm)$_2$ is obtained.

Similarly to the example 1, Sr(dpm)$_2$ is subjected to an impurity analysis due to the ICP emission spectroscopy. As the result, impurities are found to be Na=920 and K=890 (unit: ppb). In comparison with example 1, Na and K are contained much.

Example 2

Formation of SrTiO$_3$ Film Due to ALD Process that uses Sr(PrMe$_4$Cp)$_2$ (1)

ALD was conducted by: bubbling a cylinder (A) filled with Sr(PrMe$_4$Cp)$_2$ obtained in Example 1 with Ar gas at 100 sccm at 170° C.; bubbling a cylinder (B) filled with Ti(OiPr)$_4$ with Ar gas at 100 sccm at 40° C.; bubbling a cylinder (C) filled with water with Ar gas at 50 sccm at 20° C.; and flowing Ar as a purge gas at 200 sccm, under the condition of a pulse 1 sec and a purge 3 sec.

In an ALD chamber at a pressure of about 5 Torr, a Si substrate at a temperature of 300° C. was alternately subjected to 100 times of Sr cycle (A pulse-purge-C pulse-purge) and 100 times Ti cycle (B pulse-purge-C pulse-purge) to give an SrTiO$_3$ film of 10 nm thickness.

Example 3

Formation of SrTiO$_3$ Film Due to ALD Process that uses Sr(PrMe$_4$Cp)$_2$ (2)

A film is formed in a deposition chamber equipped with a chamber wall including a gas inlet port, a resistance-heating stage heater for heating a wafer and a wafer-setting lifter. The deposition chamber is connected through a pressure control valve to an exhaust pump and a cartridge heater embedded in the chamber wall is used to maintain the inside of the chamber at 160° C. Furthermore, the stage heater is set at 320° C. so that a wafer temperature may be 290° C. under substantially 0.3 Torr.

By use of a conveying arm, a Si wafer having a diameter of 300 mm is introduced from a conveying system to the deposition chamber and placed on the stage heater. Thereafter, 500 sccm of Ar gas is flowed and, by use of a pressure control valve, the pressure in the chamber is maintained at 1 Torr, followed by raising a wafer temperature.

Then, 100 g of Sr(PrMe$_4$Cp)$_2$ obtained in example is charged in a bubbling cylinder (A), kept at 165° C., followed by bubbling by flowing 50 sccm of Ar gas as a carrier gas, and thereby Sr(PrMe$_4$Cp)$_2$ vapor is obtained. Furthermore, a cylinder (B) where Ti(OiPr)$_4$ is filled is kept at 45° C., 200 sccm of Ar gas is flowed to bubble, thereby Ti(OiPr)$_4$ vapor is obtained. Still furthermore, a cylinder where water is filled as an oxidant is kept at 80° C and, with a high temperature mass flow meter disposed at an exit side, H$_2$O gas is controlled so as to flow by 200 sccm (C). Furthermore, 200 sccm of Ar is used as a purge gas.

When the raw material or oxidant is supplied (hereinafter referred to as pulse) and purged, with the respective pulses set at 5 sec and purges set at 10 sec, an ALD operation is carried out as shown below. Since, during the pulse or purge, a pressure control valve in the chamber is opened, the pressure in the chamber becomes, in accordance with the gas flow rate inside of the chamber, pulse A: 0.3 Torr, pulse B: 0.4 Torr, pulse c: 0.5 Torr and purge: 0.2 Torr. During the ALD operation, the wafer is kept at substantially 290° C.

A SrO forming cycle due to (A pulse-purge-C pulse-purge) and A TiO$_2$ forming cycle due to (B pulse-purge-C pulse-purge) are carried out 77 cycles in total at a cycle ratio of SrO/TiO$_2$=1.3. Specifically, with a series of steps of 2 cycles of (A pulse-purge-C pulse-purge), 2 cycles of (B pulse-purge-C pulse-purge), 2 cycles of (A pulse-purge-C-pulse-purge) and one cycle of (B pulse-purge-C pulse-purge) as one time, this is repeated by 11 times, and thereby, a SrTiO$_3$ film having a thickness of 5 nm is formed.

A composition of a resultant film is investigated by means of an XRF (fluorescent X-ray analysis) method and found to be Sr/Ti=1.4.

Furthermore, when, at time points when Sr(PrMe$_4$Cp)$_2$ is began to use and 90 g is used, 25 sheets are continuously deposited, average film thicknesses thereof are 53.5 and 50.3 Å, the standard deviations of in-plane film thickness distributions are 1.6 and 1.3%, and the standard deviations of interplanar film thickness distributions of 25 sheets are 2.8 and 3.3%. That is, the deposition characteristics are hardly different between the time points when Sr(PrMe$_4$Cp)$_2$ is began to use and 90 g is used, that is, a substantial end of use.

Comparative Example 5

Formation of SrTiO$_3$ Film Due to ALD Process that uses SrCp*$_2$ (1)

Except that, in place of Sr(PrMe$_4$Cp)$_2$, SrCp*$_2$ is used, a film is formed similarly to example 3.

When, at time points when 100 g of SrCp*$_2$ is began to use and 90 g is used, 25 sheets are continuously deposited, average film thicknesses thereof are 55.2 and 43.2 Å and the Sr/Ti ratio of the film is 1.4 at the start of use and 0.8 at the time point of 90 g use. That is, obviously, a supply amount of SrCp*$_2$ is deteriorated.

From example 3 and comparative example 5, since Sr(PrMe$_4$Cp)$_2$ is liquid at a bubbling temperature, from the start of use of 100 g charge amount to the end of use, vapor is stably supplied.

On the other hand, it is considered that, since SrCp*$_2$ is solid at the bubbling temperature, from the start of use of 100 g of the charge amount toward the end of use, a vaporization surface area is decreased due to aggregation of powder and heat transmission becomes insufficient due to aggregation of a raw material to a cold spot of a cylinder and a piping to result in a decrease in a supply amount of a film forming raw material, and thereby, under the same deposition conditions, a decrease in a film thickness and a deterioration in the Sr/Ti ratio are caused.

Example 4

Formation of SrTiO$_3$ Film Due to ALD Process that uses Sr(PrMe$_4$Cp)$_2$ (3)

The deposition chamber is set to conditions same as that of example 3.

Sr(PrMe$_4$Cp)$_2$ obtained in example 1 is filled in a bubbling cylinder (A) and kept at 155° C., thereto 50 sccm of Ar gas is flowed as a carrier gas to bubble, thereby Sr(PrMe$_4$Cp)$_2$ vapor is obtained. Furthermore, a cylinder (B) in which Ti(OiPr)$_4$ is filled is kept at 55° C., followed by flowing 200 sccm of Ar gas to bubble, thereby Ti(OiPr)$_4$ vapor is obtained. Still furthermore, as an oxidant, a mixed gas of O$_2$/N$_2$=500/0.5 sccm is passed through an ozonizer, thereby an O$_3$ gas having a concentration of 180 g/m$^3$ is obtained (C). Furthermore, 200 sccm of Ar is used as a purge gas.

With the pulses and purges set at 10 seconds for the A and B pulses, 2 seconds for the C pulses and 10 seconds for the purge, an ALD operation is carried out as shown below.

A SrO forming cycle due to (A pulse-purge-C pulse-purge) and a TiO$_2$ forming cycle due to (B pulse-purge-C pulse-purge) are carried out 77 cycles in total so that a SrO/TiO$_2$ cycle ratio may be 1.2. Specifically, with a series of steps of 2 cycles of (A pulse-purge-C pulse-purge), 2 cycles of (B pulse-purge-C pulse-purge), 2 cycles of (A pulse-purge-C pulse-purge), 2 cycles of (B pulse-purge-C pulse-purge), 2 cycles of (A pulse-purge-C pulse-purge) and 1 cycle of (B pulse-purge-C pulse-purge) as one time, this is repeated 7 times, thereby a SrTiO$_3$ film having a thickness of 5 nm is formed.

A composition of the resultant film is investigated by use of XRF method and found to be Sr/Ti=1.25.

Example 5

Formation of SrTiO$_3$ Film Due to ALD Process that uses Sr(PrMe$_4$Cp)$_2$ (4)

The deposition chamber is set to conditions same as that of example 3.

Sr(PrMe$_4$Cp)$_2$ obtained in example 1 is dissolved in toluene to obtain a 0.4 mol/l solution. The viscosity thereof is 40 cP.

The solution is guided by use of a liquid supply system to a vaporizer heated at 200° C., and, with 200 sccm of Ar gas as a carrier gas, at a flow rate of 0.3 g/min, while vaporizing by controlling a liquid flow meter, a Sr(PrMe$_4$Cp)$_2$ gas is obtained (A). Furthermore, Ti (OiPr)$_4$ is guided by use of a liquid supply system to a vaporizer heated at 100° C., and, with 200 sccm of Ar gas as a carrier gas, at a flow rate of 0.1 g/min, while vaporizing by controlling a liquid flow meter, a Ti(OiPr)$_4$ gas is obtained. Still furthermore, as an oxidant, a mixed gas of O$_2$/N$_2$=500/0.5 sccm is passed through an ozonizer, thereby an O$_3$ gas having a concentration of 180 g/m$^3$ is obtained (C). Furthermore, 200 sccm of Ar is used as a purge gas.

With the pulses and purges set at 2 seconds for the A and B pulses, 2 seconds for the C pulses and 5 seconds for the purge, an ALD operation is carried out as shown below.

A SrO forming cycle due to (A pulse-purge-C pulse-purge) and a TiO$_2$ forming cycle due to (B pulse-purge-C pulse-purge) are carried out 99 cycles in total so that a SrO/TiO$_2$ cycle ratio may be 1.2. Specifically, with a series of steps of 2 cycles of (A pulse-purge-C pulse-purge), 2 cycles of (B pulse-purge-C pulse-purge), 2 cycles of (A pulse-purge-C pulse-purge), 2 cycles of (B pulse-purge-C pulse-purge), 2 cycles of (A pulse-purge-C pulse-purge) and 1 cycle of (B pulse-purge-C pulse-purge) as one time, this is repeated 9 times, thereby a SrTiO$_3$ film having a thickness of 6.4 nm is formed.

When, by use of the SrTiO$_3$ film, with Ru as upper and lower electrodes, a MIM (Metal Insulator Metal) structure is formed, followed by heating at 600° C. to crystallize SrTiO$_3$, a film thickness is 0.7 nm in terms of oxide film and the leakage current when a voltage of 1 V is applied is $3.5 \times 10^{-7}$ A/cm$^2$.

Comparative Example 6

Formation of SrTiO$_3$ Film Due to ALD Process that uses SrCp*$_2$ (2)

Except that, in place of a toluene solution of Sr(PrMe$_4$Cp)$_2$ of 0.4 mol/l, a toluene solution of SrCp*$_2$ of 0.2 mol/l is used, a film is formed similarly to example 5.

A SrO forming cycle due to (A pulse-purge-C pulse-purge) and a TiO$_2$ forming cycle due to (B pulse-purge-C pulse-purge) are carried out 99 cycles in total so that a SrO/TiO$_2$ cycle ratio may be 1.2. Specifically, with a series of steps of 2 cycles of (A pulse-purge-C pulse-purge), 2 cycles of (B pulse-purge-C pulse-purge), 2 cycles of (A pulse-purge-C pulse-purge), 2 cycles of (B pulse-purge-C pulse-purge), 2 cycles of (A pulse-purge-C pulse-purge) and 1 cycle of (B pulse-purge-C pulse-purge) as one time, this is repeated 9 times, thereby a SrTiO$_3$ film having a thickness of 8.2 nm is formed.

When, by use of the SrTiO$_3$ film, with Ru as upper and lower electrodes, a MIM structure is formed, followed by heating at 600° C. to crystallize SrTiO$_3$, a film thickness is 0.9 nm in terms of oxide film and the leakage current when a voltage of 1 V is applied is $2.4 \times 10^{-3}$ A/cm$^2$.

Although the $SrTiO_3$ film is thicker in comparison with that of the $SrTiO_3$ film of example 5 in the physical film thickness and the film thickness in terms of oxide film, the leakage current is larger.

Each of the $SrTiO_3$ films of example 5 and comparative example 6 is deposited at a film thickness of 5 nm on a Si substrate and subjected to a TXRF (total reflection X-ray fluorescence) spectrometry to compare a Na content. Comparative example 6 is twice the example 5.

From this, it is considered that, since impurities such as Na are much contained in $SrCp*_2$ than in $Sr(PrMe4Cp)_2$, the electrical properties are deteriorated.

Example 6

Formation of $SrRuO_3$ Film Due to ALD Process that uses $Sr(PrMe_4Cp)_2$

In the deposition chamber, a stage heater is set at 350° C. so that a wafer temperature may be 330° C. under 0.3 Torr and other conditions are set same as that of example 3.

$Sr(PrMe_4Cp)_2$ obtained in example 1 is dissolved in toluene to obtain a 0.4 mol/l solution. The solution is guided by use of a liquid supply system to a vaporizer heated at 200° C., and, with 200 sccm of Ar gas as a carrier gas, at a flow rate of 0.3 g/min, while vaporizing by controlling a liquid flow meter, a $Sr(PrMe_4Cp)_2$ gas is obtained (A). Furthermore, $Ru(EtCp)_2$ is guided by use of a liquid supply system to a vaporizer heated at 120° C., and, with 200 sccm of Ar gas as a carrier gas, at a flow rate of 0.1 g/min, while vaporizing by controlling a liquid flow meter, a $Ru(EtCp)_2$ vapor is obtained. Still furthermore, as an oxidant, a mixed gas of $O_2/N_2=500/0.5$ sccm is passed through an ozonizer, thereby an $O_3$ gas having a concentration of $100 g/m^3$ is obtained (C). Furthermore, 200 sccm of Ar is used as a purge gas.

With the pulses and purges set at 1 second for the A and B pulses, 1 second for the C pulses and 2 seconds for the purge, an ALD operation is carried out as shown below.

A SrO forming cycle due to (A pulse-purge-C pulse-purge) and a $RuO_2$ forming cycle due to (B pulse-purge-C pulse-purge) are carried out 240 cycles in total so that a $SrO/RuO_2$ cycle ratio may be 1. Specifically, with a series of steps of 2 cycles of (A pulse-purge-C pulse-purge) and 2 cycles of (B pulse-purge-C pulse-purge) as one time, this is repeated 60 times, thereby a $SrRuO_3$ film having a thickness of 18 nm is formed.

Example 7

Formation of $SrTiO_3$ Film Due to CVD Process that uses $Sr(PrMe_4Cp)_2$

A cylinder filled with $Sr(PrMe_4Cp)_2$ obtained in Example 1 was bubbled with Ar gas at 50 sccm under about 5 Torr of inner pressure at 160° C. to supply a vapor of $Sr(PrMe_4Cp)_2$ to a CVD chamber.

At the same time, a cylinder filled with $Ti(NMe_2)_4$ was bubbled with Ar gas at 50 sccm under about 5 Torr of inner pressure at 30° C. to supply a vapor of $Ti(NMe_2)_4$ to the CVD chamber.

An oxygen gas was supplied to the CVD chamber at 100 sccm.

These gases were mixed at an inlet of the CVD chamber and introduced on a Si(100) substrate held at 2 Torr and 350° C. After 30 minutes, an $SrTiO_3$ film of 60 nm thickness was formed thereon.

Example 8

Formation of $SrRuO_3$ Film Due to CVD Process that uses $Sr(PrMe_4Cp)_2$

A cylinder filled with $Sr(PrMe_4Cp)_2$ obtained in Example 1 was bubbled with Ar gas at 50 sccm under about 7 Torr of inner pressure at 160° C. to supply a vapor of $Sr(PrMe_4Cp)_2$ to a CVD chamber.

At the same time, a cylinder filled with $Ru(EtCp)_2$ was bubbled with Ar gas at 50 sccm under about 7 Torr of inner pressure at 30° C. to supply a vapor of $Ru(EtCp)_2$ to the CVD chamber.

These gases were mixed at an inlet of the CVD chamber and introduced on a $SiTiO_3(100)$ substrate held at 2 Torr and 700° C. After 30 minutes, an $SrRuO_3$ film of 80 nm thickness was formed thereon.

What is claimed is:

1. A process for forming a strontium-containing thin film, which uses bis(propyltetramethylcyclopentadienyl)strontium having an amount of added tetrahydrofuran of not more than 9 mol % relative to a strontium atom in chemical vapor deposition or atomic layer deposition.

2. The process for forming a strontium-containing thin film according to claim 1, which uses bis(propyltetramethylcyclopentadienyl)strontium having an amount of added tetrahydrofuran of not more than 9 mol % relative to a strontium atom as an Sr source to form a $SrTiO_3$ or $(Ba,Sr)TiO_3$ film.

3. The process for forming a strontium-containing thin film according to claim 1, which uses bis(propyltetramethylcyclopentadienyl)strontium having an amount of added tetrahydrofuran of not more than 9 mol % relative to a strontium atom as an Sr source to form an $SrRuO_3$ film.

4. The process for forming a strontium-containing thin film according to claim 1, wherein bis(propyltetramethylcyclopentadienyl)strontium having an amount of added tetrahydrofuran of not more than 9 mol % relative to a strontium atom is supplied at a temperature from 130 to 350° C. by means of a bubbling method with an inert gas as a carrier gas.

5. The process for forming a strontium-containing thin film according to claim 4, wherein the inert gas is any one of Ar, $N_2$ and He.

6. The process for forming a strontium-containing thin film according to claim 4, wherein a flow rate of the inert gas is 30 to 500 sccm.

7. The process for forming a strontium-containing thin film according to claim 1, wherein bis(propyltetramethylcyclopentadienyl)strontium having an amount of added tetrahydrofuran of not more than 9 mol % relative to a strontium atom is dissolved in a solvent to prepare a solution having the viscosity of 50 cp or less, transported to a vaporizer to vaporize at a temperature from 150 to 350° C. and fed.

8. The process for forming a strontium-containing thin film according to claim 7, wherein the solvent is any one of toluene, hexane and octane.

9. The process for forming a strontium-containing thin film According to claim 1, wherein the bis(propyltetramethylcyclopentadienyl)strontium includes an amount of Na of 50 ppb or less and an amount of K of 50 ppb or less.

* * * * *